United States Patent [19]

Kapp et al.

[11] Patent Number: 4,554,914
[45] Date of Patent: Nov. 26, 1985

[54] PROSTHETIC VERTEBRAL BODY

[76] Inventors: John P. Kapp, 1933 Petit Bois N.; Robert R. Smith, 2574 Lake Cir., both of Jackson, Miss. 39211

[21] Appl. No.: 538,911

[22] Filed: Oct. 4, 1983

[51] Int. Cl.$^4$ .......................... A61F 5/04; A61F 5/00; A61F 1/04
[52] U.S. Cl. .................................. 128/92 C; 128/69; 623/17
[58] Field of Search ..................... 128/69, 92 R, 92 C, 128/92 G, 92 E; 3/1.9, 1.91

[56] References Cited

U.S. PATENT DOCUMENTS

| | | | |
|---|---|---|---|
| 2,677,369 | 5/1954 | Knowles | 128/92 |
| 2,774,350 | 12/1956 | Cleveland, Jr. | 128/92 |
| 3,030,951 | 4/1962 | Mandarino | 128/92 |
| 3,426,364 | 2/1969 | Lumb | 3/1.91 |
| 3,648,691 | 3/1972 | Lumb et al. | 128/92 D |
| 3,867,728 | 2/1975 | Stubstad et al. | 3/1.91 |
| 3,875,595 | 4/1975 | Froning | 3/1.91 |
| 3,924,276 | 12/1975 | Eaton | 3/1.91 |
| 3,987,499 | 10/1976 | Scharbach et al. | 3/1.91 |
| 4,271,836 | 6/1981 | Bacal et al. | 128/303 R |
| 4,289,123 | 9/1981 | Dunn | 128/84 R |
| 4,309,771 | 1/1982 | Patil | 3/1.91 |
| 4,369,769 | 1/1983 | Edwards | 128/69 |
| 4,401,112 | 8/1983 | Rezaian | 128/92 E |

OTHER PUBLICATIONS

Cross et al., "Acrylic Prosthesis of the Fifth Cervical Vertebra in Multiple Myeloma," *Journal of Neurosurgery*, vol. 35, Jul. 1971, pp. 112–114.
Lesoin et al., "Use of Acrylic Prosthesis for a Giant-Cell Tumor of the Cervical Spine," *Surgical Neurology*, vol. 17, No. 5, May 1982, pp. 358–360.
Ciappetta et al., "Acrylic Prosthesis of the Fifth Cervical Vertebra in Cervical Chordoma", *Clinical Neurosurgery*, 1981, vol. 83-1, pp. 35–39.
Keiro Ono et al., "Metal Prosthesis of the Cervical Vertebra", *Journal of Neurosurgery*, vol. 42, May 1975, pp. 562–566.
Yuan-zhang et al., "Radical Resection of Dorsolumbar Vertebra and Prosthetic Replacement in Giant Cell Tumor", *Chinese Medical Journal*, vol. 95(7), 1982, pp. 537–542.
F. A. Hamdi, "Prosthesis for an Excised Lumbar Vertebra," *Canadian Medical Association Journal*, vol. 100, Mar. 22 and 29, 1969, pp. 576–580.
B. Sterner, "Total Spondylectomy in Chondrosarcoma Arising from the Seventh Thoracic Vertebra," *Journal of Bone and Joint Surgery*, vol. 53B, No. 2, May 1971, pp. 288–295.
Stener et al., "Complete Removal of Three Vertebrae for Giant-Cell Tumor", *Journal of Bone and Joint Surgery*, vol. 53B, No. 2, May 1971, pp. 278–287.

*Primary Examiner*—Gene Mancene
*Assistant Examiner*—C. W. Shedd
*Attorney, Agent, or Firm*—Larson and Taylor

[57] ABSTRACT

A prosthetic vertebral body for use in a cavity left by the removal of a defective vertebral body located between two adjoining healthy vertebral bodies is disclosed. A method of replacing the defective vertebral body with the disclosed prosthetic vertebral body is also disclosed. The prosthetic vertebral body includes an adjustable support device which is located within the cavity between the two adjoining vertebral bodies for supporting and adjusting the axial spacing of the adjoining vertebral bodies. A castable material is poured into the cavity and hardens so that the adjustable support device is embedded therein. An attaching device is also provided for rigidly attaching the spinous process of the defective vertebral body to the spinous processes of the adjoining vertebral bodies. Preferably, the adjustable support device includes a pair of elongate struts whose longitudinal dimensions are adjustable. The castable material is preferably acrylic cement and the attaching device for the spinous processes are preferably a pair of elongate plates which are secured to one another and to the spinous processes.

16 Claims, 11 Drawing Figures

PROSTHETIC VERTEBRAL BODY

FIELD OF THE INVENTION

The present invention relates generally to a prosthetic vertebral body, and more particularly to a prosthetic vertebral body which is cast in place.

BACKGROUND OF THE INVENTION

The replacement of a diseased or damaged vertebral body located between adjoining healthy vertebral bodies has been disclosed in the prior art. One such method involved the placement of screws or metal rods driven into the inferior and superior vertebral bodies above and below the defective vetebral body. The screws or rods were then encased in acrylic cement which was cast in place. One problem which existed with this method is that the vertebral bodies above and below the defective vertebral body were too close together. To solve this problem, a force was used to distract the two vertebral bodies in order to restore the proper length of the spine and to correct angulation. In order to supply this force, a speading device must be placed between the two vertebral bodies and expanded. However, the cement cannot be poured and allowed to harden with the spreader in place, or the spreader will be incorporated in the hardened cement. If the spreader is removed prior to pouring, the adjoining vertebrae spring together and the desired length correction is lost. Cervical traction has been applied in a prior art method to establish the proper interspace of a removed vertebral body.

The use of an adjustable prosthesis between two adjoining vertebral bodies has also been disclosed in the prior art. In addition, the use of a posterior spinal plate to connect the spinous processes of the adjoining vertebral bodies in conjunction with the use of an expandable prosthetic vertebral body has also been disclosed.

Although a number of methods and devices have been disclosed in the prior art for replacing a diseased or damaged vertebral body, the maintaining of the proper spacing between adjoining vertebral bodies while a castable material was hardened in the cavity left by the removed vertebral body has not been possible.

SUMMARY OF THE INVENTION

In accordance with the present invention, a method and apparatus for replacing a diseased or damaged vertebral body with a prosthetic vertebral body is disclosed. The prosthetic vertebral body apparatus includes an adjustable support means which is located within the cavity between the two adjoining healthy vertebral bodies. The adjustable support means supports the adjoining vertebral bodies axially and adjusts the axial spacing of the adjoining vertebral bodies. A castable material is poured into the cavity around the adjustable support means. This castable material hardens so that the adjustable support means is embedded therein. Finally, an attaching means for rigidly attaching the spinous process of the defective vertebral body to the spinous processes of the adjoining vertebral bodies is provided.

In the preferred embodiment, the adjustable support means includes a pair of elongate struts whose longitudinal dimension is adjustable and a holding means for holding the struts at the desired longitudinal dimension. In one embodiment, each strut includes an outer sleeve having a proximal end provided with an internally threaded bore and a threaded screw having a proximal end threadably received in the bore. The distal ends of the sleeve and screw have an engagement means for engaging and holding the distal ends in a desired lateral position with respect to the adjoining vertebral bodies. Conveniently, the engagement means includes a conical point member having a laterally projecting stop on one distal end and a non-conical point member having a laterally projecting stop at the other distal end. In this manner, upon insertion of the point members with respect to the adjoining vertebral bodies, the conical point member is rotatable relative to the adjoining vertebral body while the non-conical member is non-rotatable. Thus, by rotation of the sleeve or screw containing the conical point member, the longitudinal dimension of the strut is adjusted. To make rotation of the sleeve or screw easy to accomplish, the sleeve or screw provided with the conical point has a cross-sectional shape adapted for engagement by an instrument used to rotate the sleeve or screw.

In the preferred embodiment of the present invention, the castable material is an acrylic cement. In addition, the attaching means include a pair of elongate plates which are located on respective lateral sides of the spinous processes and a securing means is provided for securing the plates to the spinous processes. Conveniently, each plate includes three spaced recesses in which the respective spinous processes are located and the securing means includes a bolt means which pass through each spinous process and adjacent plates for clamping the plates to the spinous processes. The recesses are preferably provided with lateral ridges to prevent slippage.

In another embodiment of the present invention, each strut includes a split outer sleeve having a bore therein in which an inner cylinder is provided. A ratchet means is provided between the cylinder and sleeve to allow the cylinder to move away from the sleeve. In another embodiment, the outer sleeve has a plurality of threaded holes therein and a hard ball is located below the cylinder. A plurality of set screws are threadably received in the threaded holes to push the ball progressively upward, and hence to push the cylinder progressively upward.

According to the method of the present invention, the defective vertebral body is first removed to form a cavity. Next, a spreading device is used to spread the adjoining vertebral bodies to provide the normal height of the removed vertebral body in the cavity and to correct angulation. A pair of adjustable struts are then inserted into the cavity between the adjoining vertebral bodies. These adjustable struts are extended to maintain the height of the cavity and the spreader device is removed. A castable material is then poured into the cavity which hardens into a solid block in which the struts are embedded. Finally, the spinous process of the defective vertebral body is secured to the spinous processes of the adjoining vertebral bodies.

It is an advantage of the present invention that the separation between the healthy adjoining vertebral bodies can be positively maintained while casting an acrylic resin in the cavity between the adjoining vertebral bodies.

Other features and advantages of the present invention are stated in or apparent from a detailed description of presently preferred embodiments of the invention found herein below.

DETAILED DESCRIPTION OF A PREFERRED EMBODIMENTS

Figure 1:
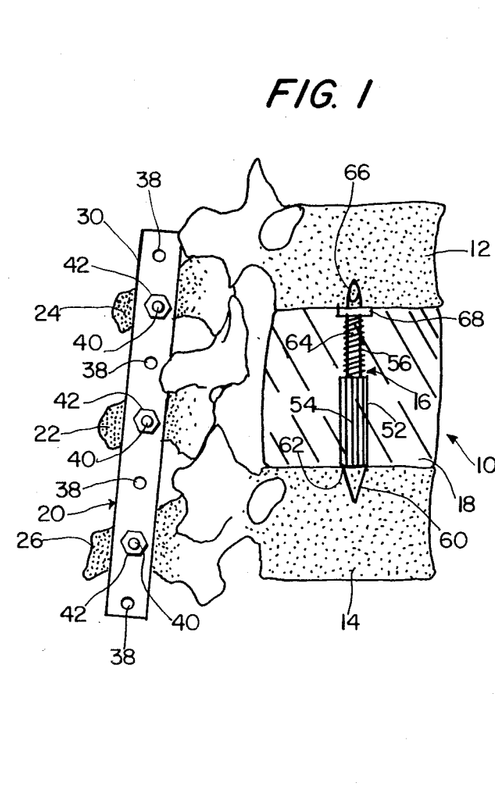
FIG. 1 is a schematic side elevational view of the prosthetic vertebral body according to the present invention.
Figure 2:
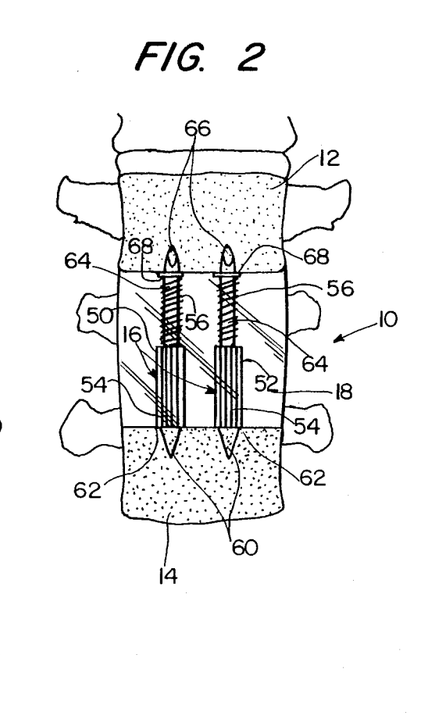
FIG. 2 is a schematic front view of the prosthetic vertebral body depicted in FIG. 1.
Figure 3:
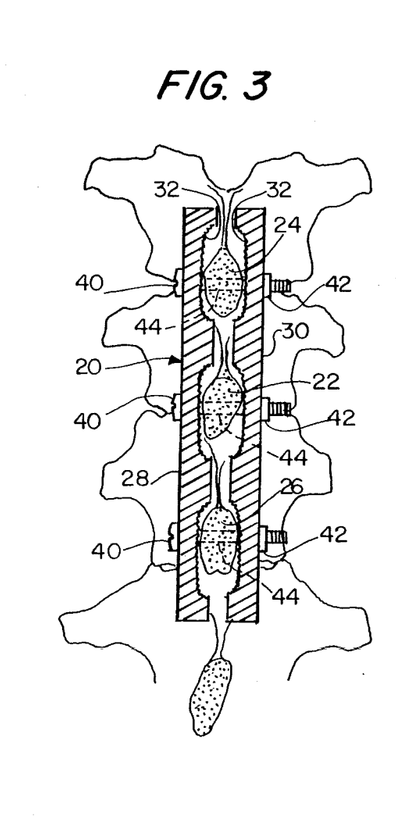
FIG. 3 is a schematic rear view in partial cross section of the prosthetic vertebral body depicted in FIG. 1.

With reference now to the drawings in which like numerals represent like elements throughout the several views, a presently preferred embodiment of a prosthetic vertebral body 10 is depicted in FIGS. 1, 2 and 3. Prosthetic vertebral body 10 is used to replace a diseased or damaged vertebral body which is located between healthy adjoining vertebral bodies 12 and 14. Prosthetic vertebral body 10 includes an adjustable support means 16, a cast material 18 in which the adjustable support means 16 is embedded, and an attaching means 20 for attaching the spinous process 22 of the defective vertebral body to the respective spinous processes 24 and 26 of the adjoining vertebral bodies 12 and 14.

Figure 4A:
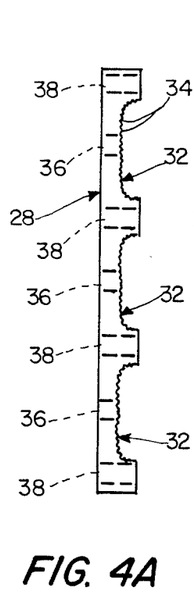
FIGS. 4a, 4b and 4c are a front view, a left side view, and a right side view, respectively, of the spinous process connecting plate depicted in FIG. 1.
Figure 4B:
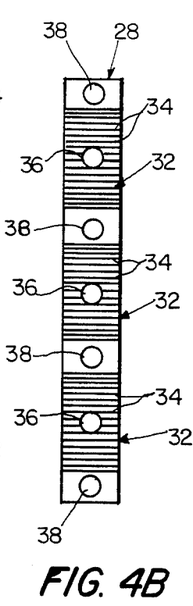
Figure 4C:
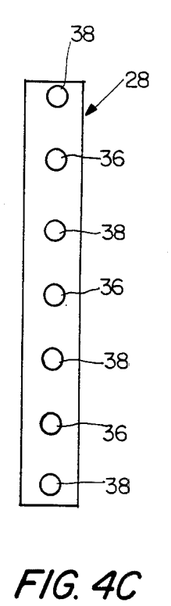

With additional reference to FIGS. 4a, 4b, and 4c, it can be seen that attaching means 20 includes a pair of elongate plates 28 and 30 which are identical to one another. Only plate 28 is depicted in FIGS. 4a, 4b and 4c. As shown, plate 28 includes three recesses 32 along the length thereof. The surfaces of recesses 32 are provided with a plurality of small ridges 34. Plate 28 is also provided with a plurality of bores 36 which pass through recesses 32, and a plurality of bores 38 which pass through the portions of plate 28 on either side of recesses 32.

Attaching means 20 also includes a plurality of bolts 40 and nuts 42. As depicted in FIGS. 1 and 3, bolts 40 pass through respective bores 36 in plates 28 and 30 and through respective bores 44 provided in spinous processes 22, 24 and 26. Nuts 42 are then threadably attached to the ends of bolts 40 passing through plate 30. By means of bolts 40 and nuts 42, plates 28 and 30 are securely attached to spinous processes 22 24, and 26.

As shown in FIG. 2, adjustable support means 16 preferably includes two adjustable strut members 50 and 52. Adjustable strut member 50 is depicted in greater detail in FIGS. 5a and 5b. Both adjustable strut members 50 and 52 are identical so that only strut 50 will be described in detail with the same elements of strut 52 identified with the same numerals.

Figure 5A:
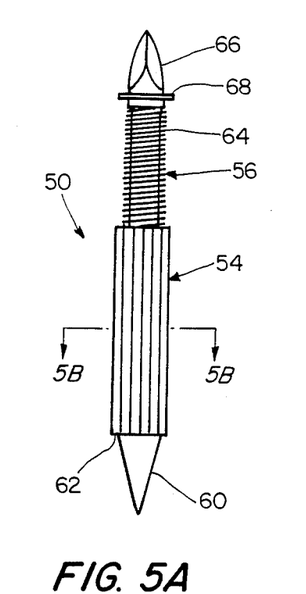
FIGS. 5a and 5b are a front view and a cross-sectional top view of a strut depicted in FIG. 1.
Figure 5B:
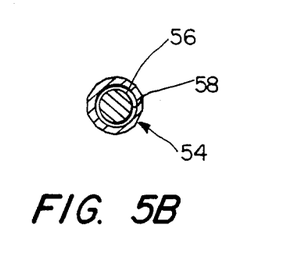

Adjustable strut member 50 includes two components, an outer sleeve 54 and a screw 56. Outer sleeve 54 is provided with an internal bore 58 which is suitably threaded to receive screw 56. As shown best in FIG. 5b, the outer periphery of outer sleeve 54 is shaped to be rotated by a suitable tool (not shown). Located at the distal end of outer sleeve 54 is a conical point 60. The maximum diameter of conical point 60 is less than the outside diameter of outer sleeve 54 such that a shoulder or stop 62 is provided.

Screw 56 includes a threaded portion 64 and a distal end containing an arrow point 66. Arrow point 66 is generally wedge shaped so as not to be symmetrical about the longitudinal axis of screw 56. Located between point 66 and threaded portion 64 is a laterally extending stop 68.

As shown best in FIGS. 1 and 2, a cast material 18 is located between vertebral bodies 12 and 14. In the preferred embodiment of the present invention, cast material 18 is an acrylic cement.

The method of replacing a defective vertebral body located between adjoining healthy bodies 12 and 14 with a prosthetic vertebral body 10 according to the present invention is as follows. Initially, the remains of the defective vertebral body are removed from between the two healthy vertebral bodies 12 and 14 to form a cavity. Insofar as the surgical procedure is concerned to accomplish this, the patient is positioned on his side. An incision is then made over or parallel to a rib which crosses the midlline of the back. The muscles are cut to expose the spinous processes, lamina, pedicle, and either the rib (in the thoracic area) or the transverse process of the vertebrae (in the lumbar area). The rib or transverse process adjacent the spine is then removed. Finally, the diseased or collapsed remains of the vertebral body to be replaced are removed so that a cavity is formed.

After the cavity is formed, a spreader is inserted between the opposing surfaces of the adjacent healthy vertebral bodies 12 and 14 to distract vertebral bodies 12 and 14 and to restore the normal height of the vertebral body to be replaced in the cavity. The spreader is also used to correct any angulation of the spine caused by the collapse of the vertebral body which has been removed.

With the spreader still in place, strut members 50 and 52 are inserted in the cavity. Before insertion, screw 56 has been screwed down into outer sleeve 54 so that the height of strut member 50 and 52 is slightly smaller than the length of the cavity in which strut members 50 and 52 are inserted. Once strut members 50 and 52 are in position in the cavity, respective outer sleeves 54 are turned relative to screws 56 to increase the longitudinal lengths of strut members 50 and 52. This causes points 60 and 66 to be inserted into respective vertebral bodies 14 and 12.

It should be noted that due to the wedge shape of arrow point 66, as arrow point 66 enters vertebral body 12 both arrow point 66 and screw 56 are prevented from rotating. However, as conical point 60 enters vertebral body 14, conical point 60 can rotate relative to vertebral body 14 and hence does not prevent outer sleeve 54 from rotating. Therefore, the overall length of adjustable strut members 50 and 52 can be increased as desired by further rotation of outer sleeve 54. It should also be noted that points 60 and 66 are driven into respective vertebral bodies 14 and 12 until stops 62 and 68 contact respective vertebral bodies 14 and 12. At this time, strut members 50 and 52 are secured in place in the cavity and can maintain the separation of vertebral bodies 12 and 14 which the spreader created. In addition, further rotation of outer sleeves 54 can be used to additionally adjust the separation of vertebral bodies 12 and 14 as desired. At this time, therefore, the spreader is removed.

With the spreader removed and strut members 50 and 52 maintaining the proper height of the cavity, a castable material is poured into the cavity. The castable material hardens into a solid block of cast material 18 in which strut members 50 and 52 are embedded. In this manner, cast material 18 is positively and permanently located in the cavity between vertebral bodies 12 and 14, and the height of cast material 18 is precisely the height formerly provided by the defective vertebral body which has been removed.

Due to the removal of the defective vertebral body, spinous process 22 of the removed vertebral body must also be secured in place. In order to accomplish this, attaching means 20 is used. Initially, bores 44 are drilled in spinous processes 22, 24, and 26. Next, plates 28 and 30 are located so that recesses 32 are provided on either side of spinous processes 22, 24, and 26. Bolts 40 are then inserted through bores 36 and 44 as shown in FIG. 3. Finally, nuts 42 are threaded onto bolts 40 and tightened to securely hold spinous processes 22, 24, and 26 rigidly removable with respect to each other. It should be noted that ridges 34 provided in recesses 32 help prevent any longitudinal movement of spinous processes 22, 24, or 26 relative to one another.

Although attaching means 20 has been described as using bolts 40 which pass through spinous processes 22, 24 and 26, it should also be appreciated that plates 28 and 30 can be securely clamped to spinous processes 22, 24, and 26 by bolts 40 which do not pass through spinous processes 22, 24, and 26. In this embodiment, four bolts 40 pass through bores 38 which are located above or below respective spinous processes 22, 24, and 26. Nuts 42 are then threaded onto bolts 40 to securely draw plates 28 and 30 toward one another and to clamp spinous processes 22, 24, and 26 therebetween. Again, spinous processes 22, 24, and 26 are located in recesses 32 and ridges 34 additionally prevent any longitudinal movement of spinous processes 22, 24, or 26 relative to one another.

Figure 6:
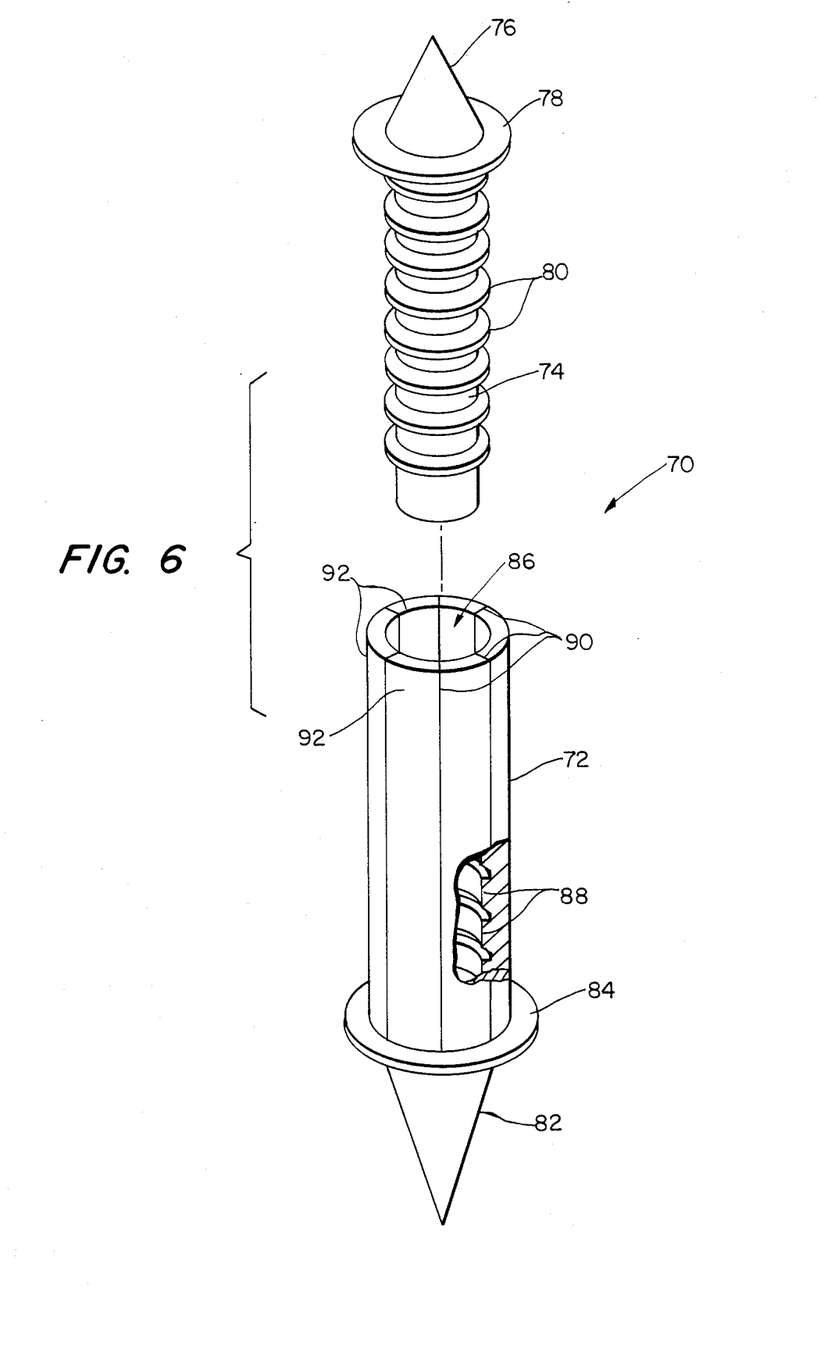
FIG. 6 is a prospective view of an alternative embodiment of a strut according to the present invention.

Depicted in FIG. 6 is an alternative embodiment of an adjustable strut member 70. Adjustable strut member 70 includes an outer sleeve 72 and an inner cylinder 74. Inner cylinder 74 includes a distal end having a conical point 76 and a laterally extending stop 78. Located at spaced intervals along the length of inner cylinder 74 below stop 78 are a plurality of circumferential teeth 80.

Outer sleeve 72 is provided with a conical point 82 at the distal end thereof and a laterally extending stop 84 adjacent thereto. Outer sleeve 72 also includes a central bore 86 in which inner cylinder 74 is received. As shown, bore 86 is provided with a plurality of upwardly inclined teeth 88 which are spaced at the same intervals as teeth 80. Outer sleeve 72 is also provided with radial slots 90 along the length of bore 86 so that outer sleeve 72 is split into a plurality of resilient segments 92.

It should be appreciated that teeth 80 and 88 provide adjustable strut members 70 with a ratchet means by which inner cylinder 74 can be progressively extended and held in place relative to outer sleeve 72. Thus, adjustable strut member 70 is used in the same manner as adjustable strut members 50 and 52 described above. It should also be appreciated that initially inner cylinder 74 is located in bore 86 of outer sleeve 72 with stop 78 adjacent the top of outer sleeve 72. Thus, adjustable strut member 70 is inserted between adjoining vertebral bodies 12 and 14, a suitable tool or the like is used to move stop 78 away from stop 84. In this manner, conical points 76 and 82 are pushed into adjoining vertebral bodies 12 and 14. As inner cylinder 74 moves relative to outer sleeve 72, teeth 80 on inner cylinder 74 slide up and rest on top of teeth 88 which are inclined in the direction of movement. The mating surfaces of teeth 80 and 88 are flat to provide a positive locking mechanism preventing inner cylinder 74 from traveling back into bore 86 of outer sleeve 72. To facilitate the upward movement of inner cylinder 74, slots 90 cause segments 92 to be resiliently mounted relative to move slightly outward as teeth 80 of inner cylinder 74 contact the inclined portions of teeth 88 in bore 86 of outer sleeve 72.

Figure 7:
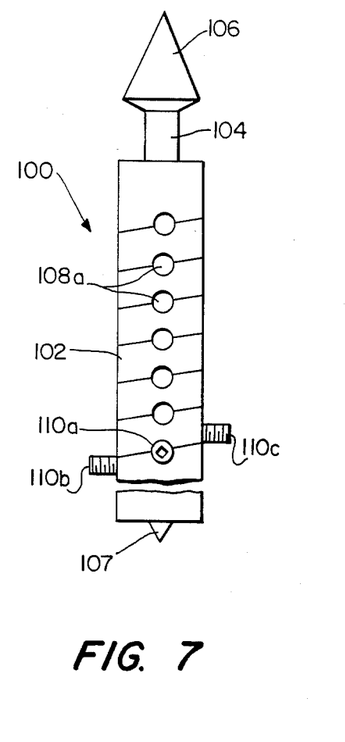
FIGS. 7 and 8 are a front view and a cross-sectional front view of another alternative embodiment of a strut according to the present invention.
Figure 8:
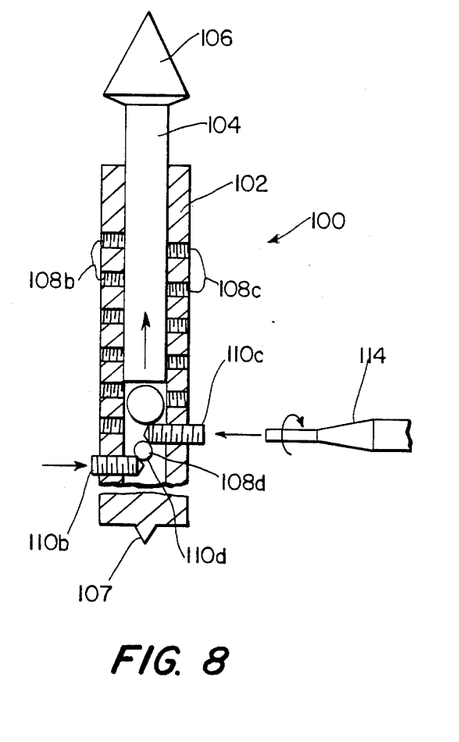

Depicted in FIGS. 7 and 8 is still another embodiment of an adjustable strut member 100. Adjustable strut member 100 includes an outer sleeve 102 and an inner cylinder 104. As shown, inner cylinder 74 includes a conical point 106 at the distal end thereof. Outer sleeve 72 also includes a conical point 108.

Located along the length of outer sleeve 102 are four rows of threaded holes 108a, 108b, 108c and 108d. As shown, the rows of threaded holes 108a, 108b, 108c, and 108d are staggered with respect to one another so that an upward spiral is provided around outer sleeve 102 by the pattern of threaded holes 108a, 108b, 108c, and 108d.

Received in one of threaded holes 108a, 108b, 108c, and 108d are set screws 110a, 110b, 110c, and 110d, respectively. As shown, set screws 110 have pointed ends 112 and are turnable by a suitable tool 114. Located inside of outer sleeve 102 below inner cylinder 104 is a ball 116 made of a suitable hard material such as metal.

In operation, adjustable strut member 100 is used in much the same manner as adjustable strut members 50 and 52. However, in order to move inner cylinder 104 relative to outer sleeve 102, set screws 110 are used. Thus, as seen best in FIG. 8, as set screws 110a, 110b, 110c, and 110d are sequentially inserted into outer sleeve 102, ball 116 is forced upward by the insertion of each surrounding screw. As ball 116 is forced upward, inner cylinder 104 is similarly forced upward so that conical point 106 and conical point 107 engage respective adjoining vertebral bodies 12 and 14. After all four set screws 110 have been inserted, the three set screws not engaging ball 116 are removed and moved to the succeeding threaded hole 108a, 108b, 108c, or 108d. Thus, further raising of inner cylinder 104 relative to outer sleeve 102 is possible by again inserting appropriate set screws 110a, 110b, 110c, or 110d into threaded holes 108a, 108b, 108c, or 108d.

Although three different types of adjustable strut members have been described for use with the present invention, it should be appreciated by those of ordinary skill in the art that other designs for adjustable strut members are possible. In addition, other castable materials in addition to acrylic cement are possible. Finally, various types of attaching means for the spinous processes can also be used.

Thus, while the present invention has been described with respect to exemplary embodiments thereof, it will be understood by those of ordinary skill in the art that variations and modifications are possible within the scope and spirit of the invention.

We claim:

1. A prosthetic vertebral body for use in a cavity left by the removal of a defective vertebral body located between adjoining healthy vertebral bodies comprising:
   an adjustable support means which is locatable totally within the cavity between the two adjoining vertebral bodies for supporting the adjoining vertebral bodies axially and for adjusting the axial spacing of the adjoining vertebral bodies;

a cast material which is poured in the cavity and which hardens such that said adjustable support means is embedded therein; and an attaching means for rigidly attaching the spinous process of the defective vertebral body to the spinous processes of the adjoining vertebral bodies.

2. A prosthetic vertebral body as claimed in claim 1 wherein said adjustable support means includes a pair of elongate struts whose longitudinal dimension is adjustable and a holding means for holding said struts at a desired longitudinal dimension.

3. A prosthetic vertebral body as claimed in claim 2 wherein each said strut includes an outer sleeve having a proximal end provided with an internally threaded bore and a screw having a proximal end which is threadably received in said bore of said sleeve, the distal ends of said sleeve and said screw having an engagement means for engaging and holding said distal ends in a desired lateral position with respective adjoining vertebral bodies.

4. A prosthetic vertebral body as claimed in claim 3 wherein said engagement means includes a conical point member having a laterally projecting stop located proximally adjacent thereto at one distal end, and a non-conical point member having a laterally projecting stop located proximally adjacent thereto at the other distal end such that upon insertion of said point members in respective adjoining vertebral bodies said conical point member is rotatable relative to the adjoining vertebral body while said non-conical member is non-rotatable relative to the adjoining vertebral body and said point members are inserted in the adjoining vertebral bodies until said laterally projecting stops contact the adjacent adjoining vertebral bodies.

5. A prosthetic vertebral body as claimed in claim 4 wherein said conical point member is located on said sleeve and wherein said sleeve has a cross-sectional shape adapted for engagement by an instrument used for rotating said sleeve relative to said screw.

6. A prosthetic vertebral body as claimed in claim 2 wherein said cast material is acrylic cement.

7. A prosthetic vertebral body as claimed in claim 2 wherein said attaching means includes a pair of elongate plates which are located on respective lateral sides of the spinous processes and a securing means for securing said plates to the spinous processes.

8. A prosthetic vertebral body as claimed in claim 7 wherein each said plate includes three spaced recesses in which the respective spinous processes are located, and wherein said securing means includes three bolt means which pass through respective spinous processes and adjacent said plates for clamping said plates to the spinous processes.

9. A prosthetic vertebral body as claimed in claim 8 wherein said recesses are longer longitudinally than the longitudinal dimension of each spinous process and said recesses include a plurality of small lateral ridges along the longitudinal length thereof to prevent the spinous processes from slipping relative to said plates after said plates are clamped by said bolt means.

10. A prosthetic vertebral body as claimed in claim 2 wherein each said strut includes an outer sleeve having a proximal end provided with a bore which sleeve is split longitudinally along the length of said bore, an inner cylinder having a proximal end which is received in said bore of said sleeve, a ratchet means for allowing said cylinder to move distally relative to said sleeve and for preventing said cylinder from moving proximally relative to said sleeve including proximally inclined teeth located peripherally on one of said sleeve in said bore and said cylinder and mating teeth peripherally located on the other of said sleeve in said bore and said cylinder, and an engagement means located on the distal ends of said sleeve and said cylinder for engaging and holding said distal ends in a desired lateral position with respective adjoining vertebral bodies.

11. A prosthetic vertebral body as claimed in claim 10 wherein said engagement means includes a conical point member having a laterally projecting stop located proximally adjacent thereto at the distal ends of said sleeve and said cylinder.

12. A prosthetic vertebral body as claimed in claim 2 wherein each said strut includes an outer sleeve having a proximal end provided with a bore and with a plurality of threaded holes longitudinally spaced along the length of said bore, an inner cylinder having a proximal end which is received in said bore of said sleeve, a plurality of set screws which are threadably received in said threaded holes, a hard ball which has a diameter approximately equal to the diameter of said inner cylinder and which is located in said bore adjacent the proximal end of said cylinder such that the insertion of said set screws through said threaded holes and into said bore progressively toward the proximal end of said sleeve causes said ball and hence proximal end of said inner cylinder to be moved progressively toward the proximal end of said sleeve, and an engagement means located on the distal ends of said sleeve and said cylinder for engaging and holding said distal ends in a desired lateral position with respective adjoining vertebral bodies.

13. A method of replacing a defective vertebral body located between adjoining healthy vertebral bodies with a prosthetic vertebral body comprising the steps of:

removing the remains of the defective vertebral body to form a cavity;

spreading the adjoining vertebral bodies with a spreading device to provide the normal height of the removed vertebral bodying in the cavity;

inserting a pair of adjustable struts within the cavity and between the adjoining vertebral bodies;

extending the adjustable struts to maintain the height of the cavity;

removing the spreader device;

pouring a castable material into the cavity which hardens into a solid block with the struts embedded therein; and securing the spinous process of the defective vertebral body to the spinous processes of the adjoining vertebral bodies.

14. A method of replacing a defective vertebral body as claimed in claim 13 wherein the castable material is an acrylic cement.

15. A method of replacing a defective vertebral body as claimed in claim 13 wherein each strut includes an outer sleeve having a proximal end provided with an internally threaded bore and a screw having a proximal end which is threadably received in the bore of the sleeve, the distal end of one of the sleeve and screw having a conical poinit member and a laterally projecting stop located proximally adjacent thereto and the other of the sleeve and screw having a non-conical point member and a laterally projecting stop located proximally adjacent thereto; and wherein the extending of the adjustable struts includes the steps of rotating the one of the sleeve and screw having the conincal point member relative to the other to cause the distal ends to move further away from one another and the respective point members to advance into the adjoining vertebral body until the respective stop contacts the respective adjoining vertebral body.

16. A method of replacing a defective vertebral body as claimed in claim 13 wherein the securing of the spinous processes includes the placing of a pair of elongate plates on each lateral side of the spinous processes and the clamping together of the plates to hold the spinous processes immovably therebetween.

* * * * *